(12) United States Patent
Liou

(10) Patent No.: US 6,341,956 B1
(45) Date of Patent: *Jan. 29, 2002

(54) DENTAL DISTRACTOR

(76) Inventor: Eric Jein-Wein Liou, No. 199, Tun-Hwa North Rd., Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 09/587,342

(22) Filed: Jun. 5, 2000

(51) Int. Cl.$^7$ ................................................ A61C 3/00
(52) U.S. Cl. ............................ 433/18; 433/17; 433/22
(58) Field of Search .................... 433/7, 12, 17, 433/18 OR, 23, 22

(56) References Cited

U.S. PATENT DOCUMENTS

| | | | | |
|---|---|---|---|---|
| 382,897 A | * | 1/1888 | Patrick | 433/18 |
| 618,105 A | * | 1/1899 | Knapp | 433/17 |
| 4,424,031 A | * | 1/1984 | Dahan | 433/18 |
| 4,483,674 A | * | 11/1984 | Schutz | 433/22 |
| 5,645,423 A | * | 7/1997 | Collins, Jr. | 433/18 |
| 5,873,715 A | * | 2/1999 | Liou | 433/18 |

* cited by examiner

Primary Examiner—John J. Wilson
(74) Attorney, Agent, or Firm—Troxell Law Office PLLC

(57) ABSTRACT

An orthodontic dental distractor was invented for rapid orthodontic tooth movement and leveling treatment. The molars at two side of patients teeth are mounted respectively with a barrel band which fastens to a steel wire which in turn engages with the brackets adhered to the front teeth like a conventional orthodontic treatment does. However the dental distractor further includes a front joint member which has a holding member to engages with one end of the steel wire, a rear joint member which has a hook to engage with the barrel band and a screw bar which engage with the front end and rear joint member. Turning the screw bar, the front joint member will be moved toward the rear joint member for pulling or pushing the bracket, consequently moving the front teeth toward or away from the molar for leveling the teeth.

2 Claims, 6 Drawing Sheets

DENTAL DISTRACTOR

BACKGROUND OF THE INVENTION

1. Field of the Invention

This invention relates to a dental distractor or and particularly to a dental distractor for rapidly correcting severe front teeth crowding and protrusion in orthodontic treatment.

2. Description of the Prior Art

Front teeth crowding and protrusion is an unsightly defect happened to many people. An orthodontic treatment is usually needed to correct this defect. For some other reasons, such like after making some specific dental operations, orthodontic treatments may also be needed to correct teeth problems.

Although there are many reasons which may need to proceed orthodontic treatments, we only take one example to illustrate the steps for performing a conventional orthodontic treatment. Hereunder is an example to perform a conventional orthodontic treatment for severe anterior teeth crowding or protrusion. Such a conventional orthodontic treatment generally includes the following steps:

1. Dental operation (for example, extracting the first premolars or other operation).
2. Mounting a barrel band on the molar and having a steel wire bore formed on a side wall of the barrel band.
3. Adhering a bracket on the surface of the anterior teeth to be treated and having a steel wire slot formed on a sidewall of the bracket.
4. Initial teeth leveling by engaging a steel wire between the steel wire bore and the steel wire slot under desirable tension. Depending on the alignment of teeth, this step may last about three to six months.
5. Retracting canine backward to make room for anterior teeth alignment and leveling. This step may last about four to six months for children and seven to eight months for adults.
6. Retracting anterior teeth to level the protruding teeth. This step may last about six months.
7. Fine adjustment of occlusion and tooth angulations. This step may take about three to six months.

Total conventional orthodontic treatment time thus will take one and a half to two years. It is too long a time for most patients. It is not esthetic to wear braces for such a long period and it is very burdensome for the patients to maintain their oral hygiene as well. It also is very inconvenient and time-consuming for the patients to visit orthodontist's office to make periodical adjustment in such a long period.

Same applicant has been disclosed a dental distractor (U.S. Pat. No. 5,873,715) which can reduce orthodontic treatment time. However, it has the deficiency of being too complicated and bulky in structure. It is particularly annoying to put it in the mouth which is delicate and sensitive (for example, the mouth after dental operation). It is prone to hurt mucosa and even causes oral ulcer. Moreover, the dental distractor disclosed in U.S. Pat. No. 5,873,715 can not be used together with conventional steel wire treatment (e.g., use steel wire to correct teeth alignment as mentioned above). Thus, there is still a room for further improvement.

SUMMARY OF THE INVENTION

It is an object of this invention to provide a dental distractor that can greatly reduce orthodontic treatment time to alleviate patients trouble and inconvenience. In addition, the dental distractor disclosed in this invention should also be able to use together with steel wire treatment.

It is another object of this invention to provide a dental distractor that can either pull two teeth toward each other for correcting teeth having gap therebetween, or push teeth away from each other for correcting teeth being too crowded.

This invention may be used for correcting front teeth crowding or teeth alignment correcting after dental surgery or too large gap between teeth with or without the first premolar extracted.

According to a preferred embodiment of this invention, the molar at two sides of the patient are mounted respectively with a barrel band which has a steel wire bore and an engaging bore formed on a side wall thereof. The anterior teeth have conventional brackets adhered thereon. Each bracket has a steel wire slot. Then a steel wire is engaged with the steel wire slots and has its two ends fastened to the steel wire bores. The dental distractor of this invention has a front joint member, a rear joint member and a screw bar. The front joint member has a round hole member passing through one end of the screw bar and a holding member engageable with one end of the steel wire. The rear joint member has a screw body engageable with another end of the screw bar and a C-shaped hook engageable with the engaging bore of the molar bracket. The screw bar has a screw head for turning the screw bar so that the front joint member may be moved toward the rear joint member. Consequently the steel wire will be pulled and move the anterior teeth for correcting purpose.

In another aspect of this invention, the C-shaped hook is mounted on the front joint member while the rear joint member has a plurality of holding members for engaging with the steel wire. Turning the screw bar will move the rear joint member toward (away from) the front joint for teeth correction and leveling.

BRIEF DESCRIPTION OF THE DRAWINGS

The following description and draws show the invention, as well as its many advantages.

DETAILED DESCRIPTION OF THE PREFERRED EMBODIMENT

Figure 1A:
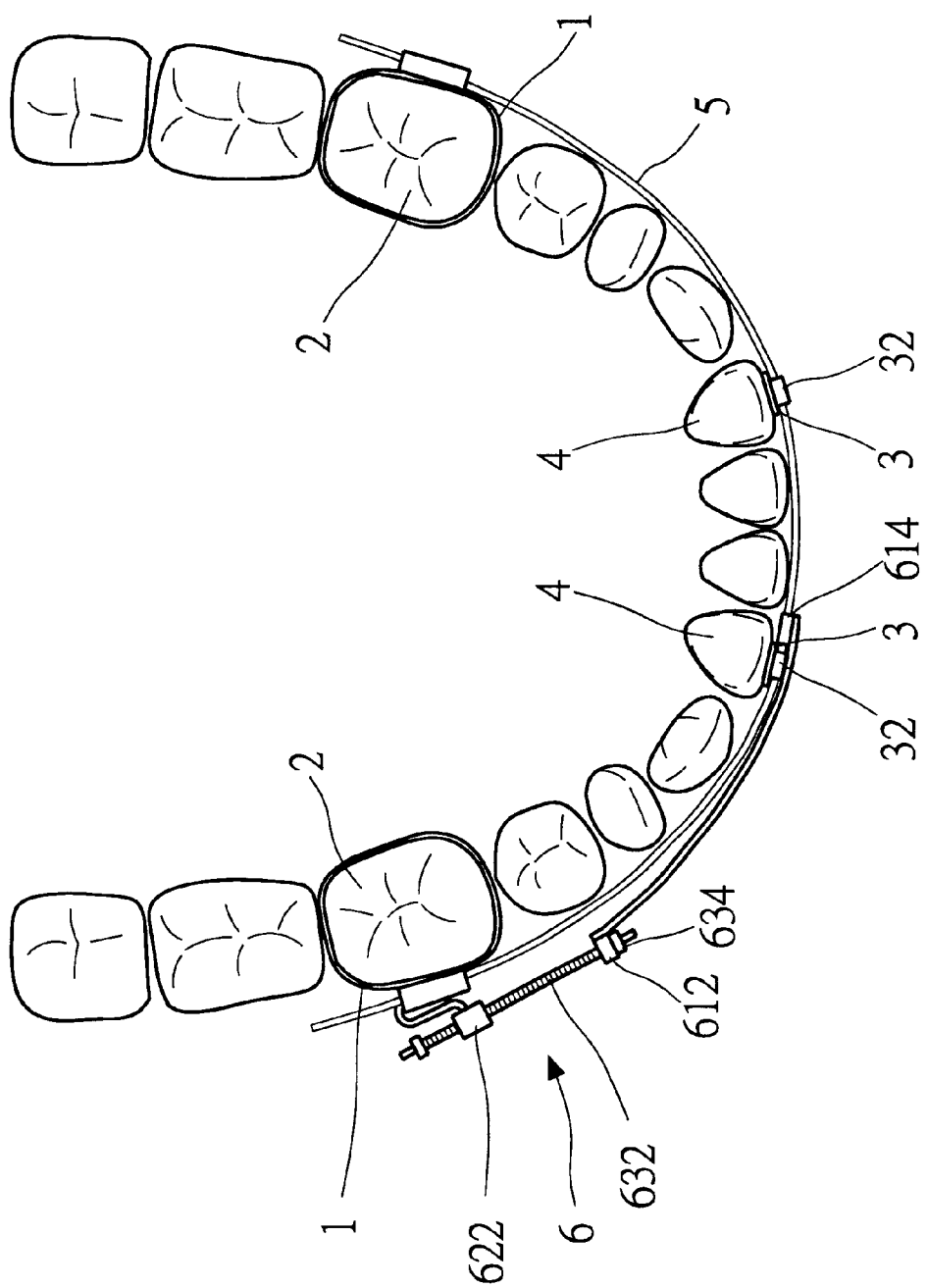
FIG. 1A is a top view of a first embodiment of this invention.
Figure 1B:
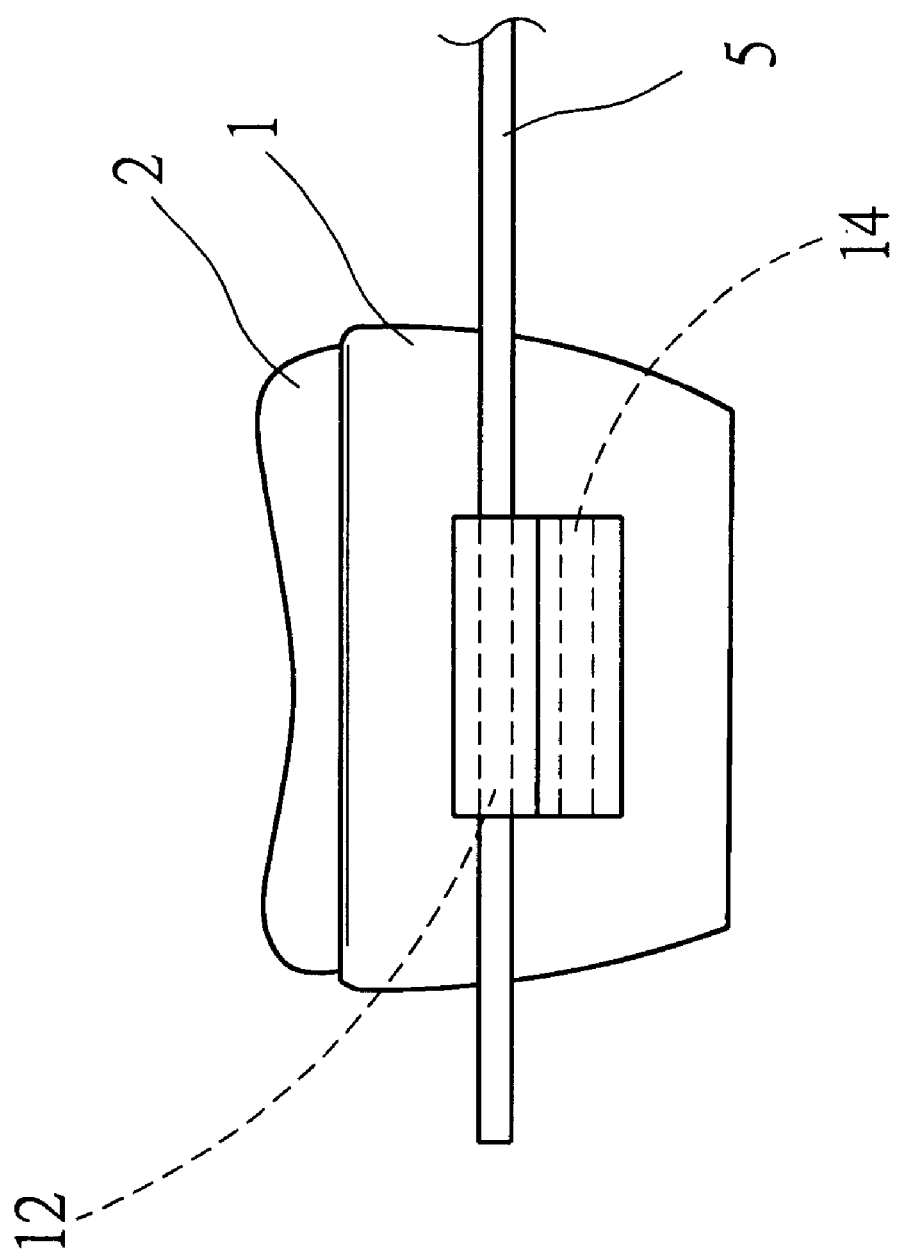
FIG. 1B is an enlarged fragmentary view of FIG. 1A showing the barrel band of the present invention.
Figure 2:
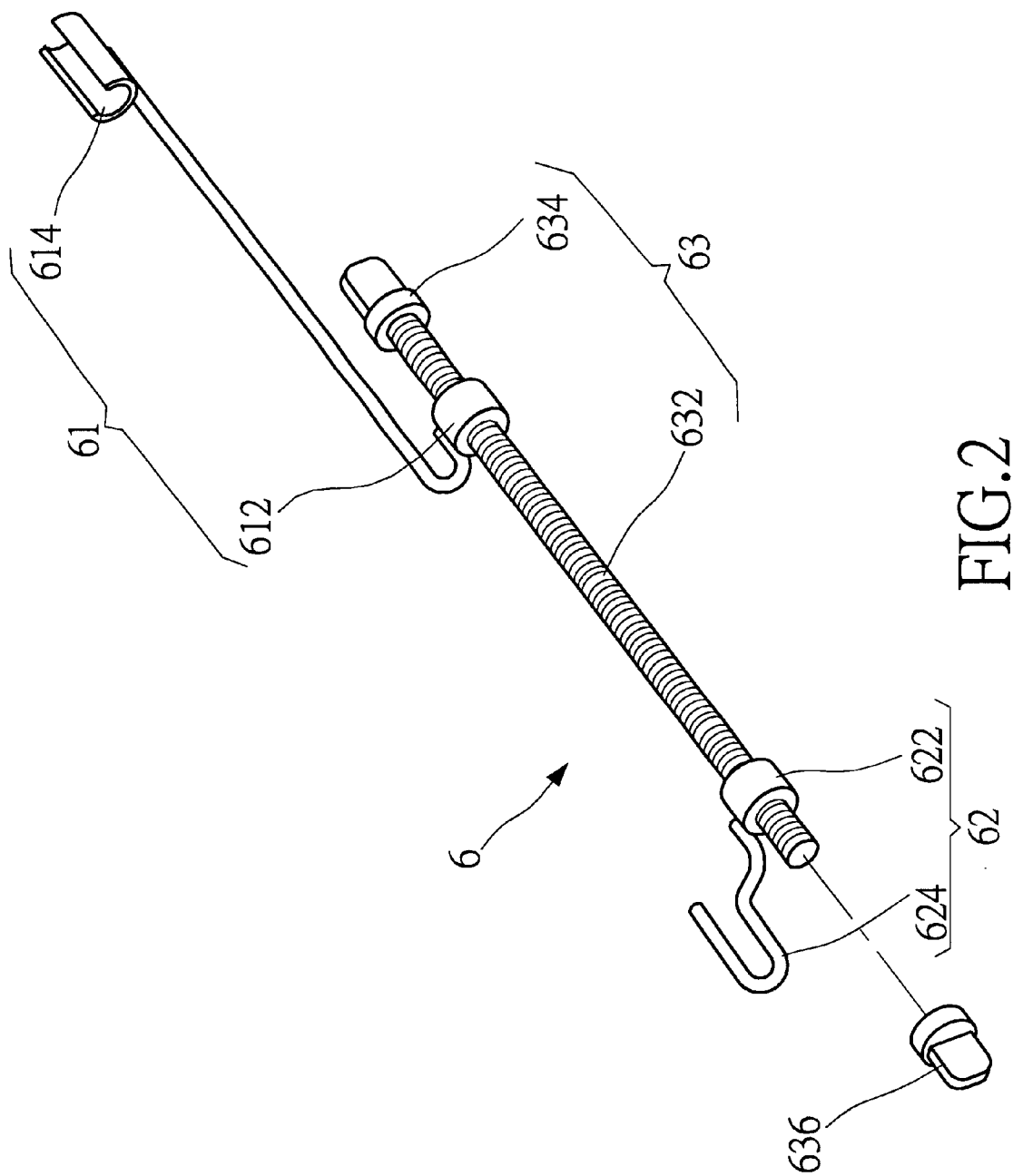
FIG. 2 is a fragmentary perspective view of the first embodiment shown in FIG. 1.

The first embodiment shown in FIGS. 1A, 1B and 2 is to correct teeth which have gap therebetween.

Referring to FIGS. 1A and 1B, in this invention the molar 2 on both side of the patient have respectively a barrel band 1 mounted thereon. Each barrel band 1 has a steel bore 12 and an engaging bore 14 formed on a side wall thereof. On the anterior teeth 4, there are a plurality of brackets 3 adhered to like conventional orthodontic treatment do. Each bracket has a steel wire slot 32 formed therein. A steel wire 5 is passed through and engaged with the steel wire slot 32 and has its two ends fastened to the steel wire bore 12.

Referring to FIG. 2, the dental distractor 6 of the present invention includes a front joint member 61, a rear joint member 62 and a screw bar 63. The front joint member 61 has a round hole member 612 and a holding member 614 engageable with the steel wire 5 at a location adjacent to the steel wire slot 32. The rear joint member 62 has a screw body 622 and a C-shaped hook 624 engageable with the engaging bore 14. The screw bar 63 has a screw bar stem 632 which has one end engageable with the screw body 622 and another end passing through the round hole member 612 and attached to a screw head 634. The other end of the screw bar 63 which is near to the rear joint member 62 can also be provided with another screw head 636. Thus when the screw head 634 is turned, the front joint member 61 may be pushed by the screw head 634 and moved toward the rear joint member 62. As the rear joint member 62 in anchored to the molar 2 by the hook 624 and the barrel band 1, the holding member 614 will pull the brackets 3 and consequently the anterior teeth 4 toward the molar 2 for leveling the protrusive anterior teeth or narrowing large teeth gap.

Figure 3A:
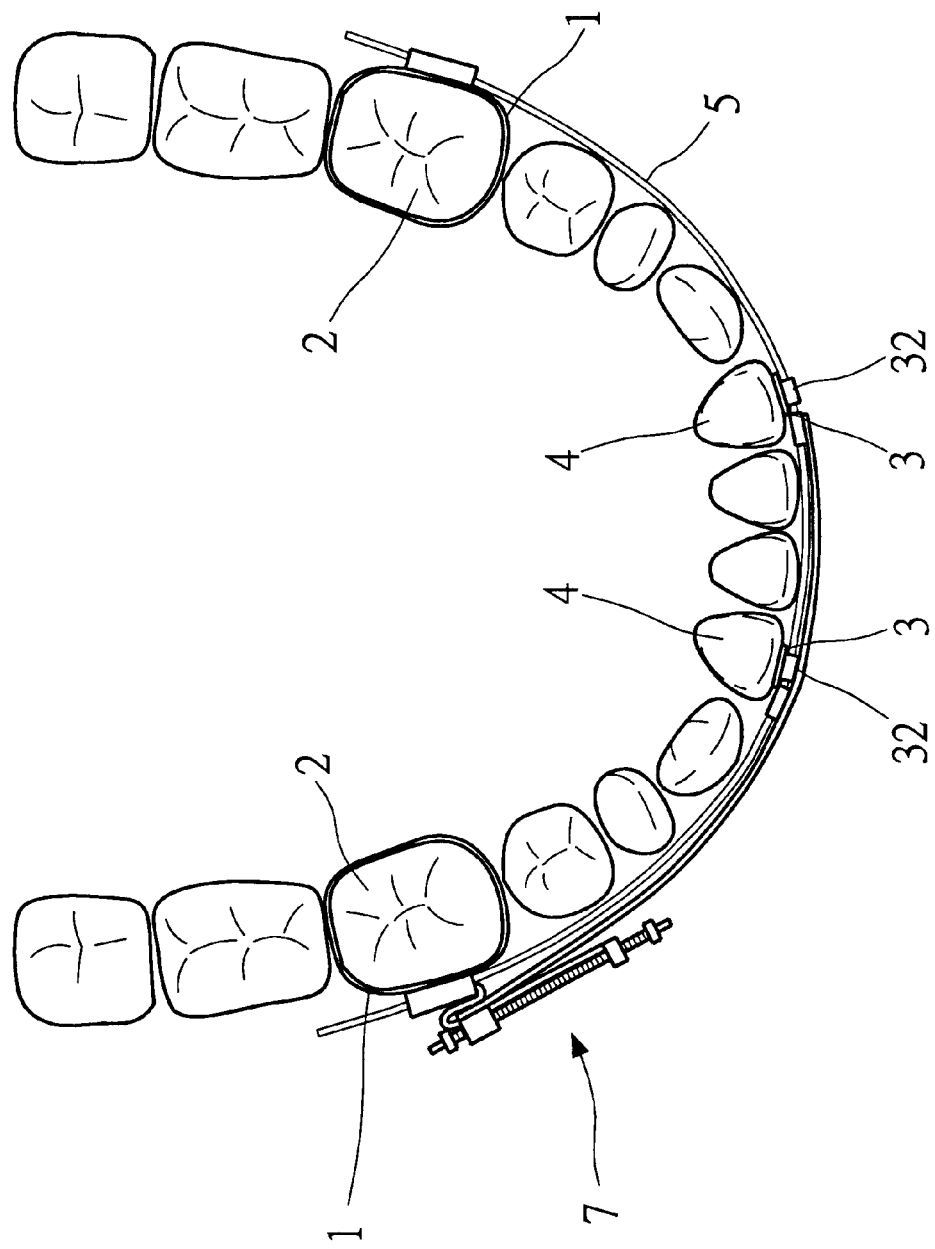
FIG. 3A is a top view of a second embodiment of this invention.
Figure 3B:
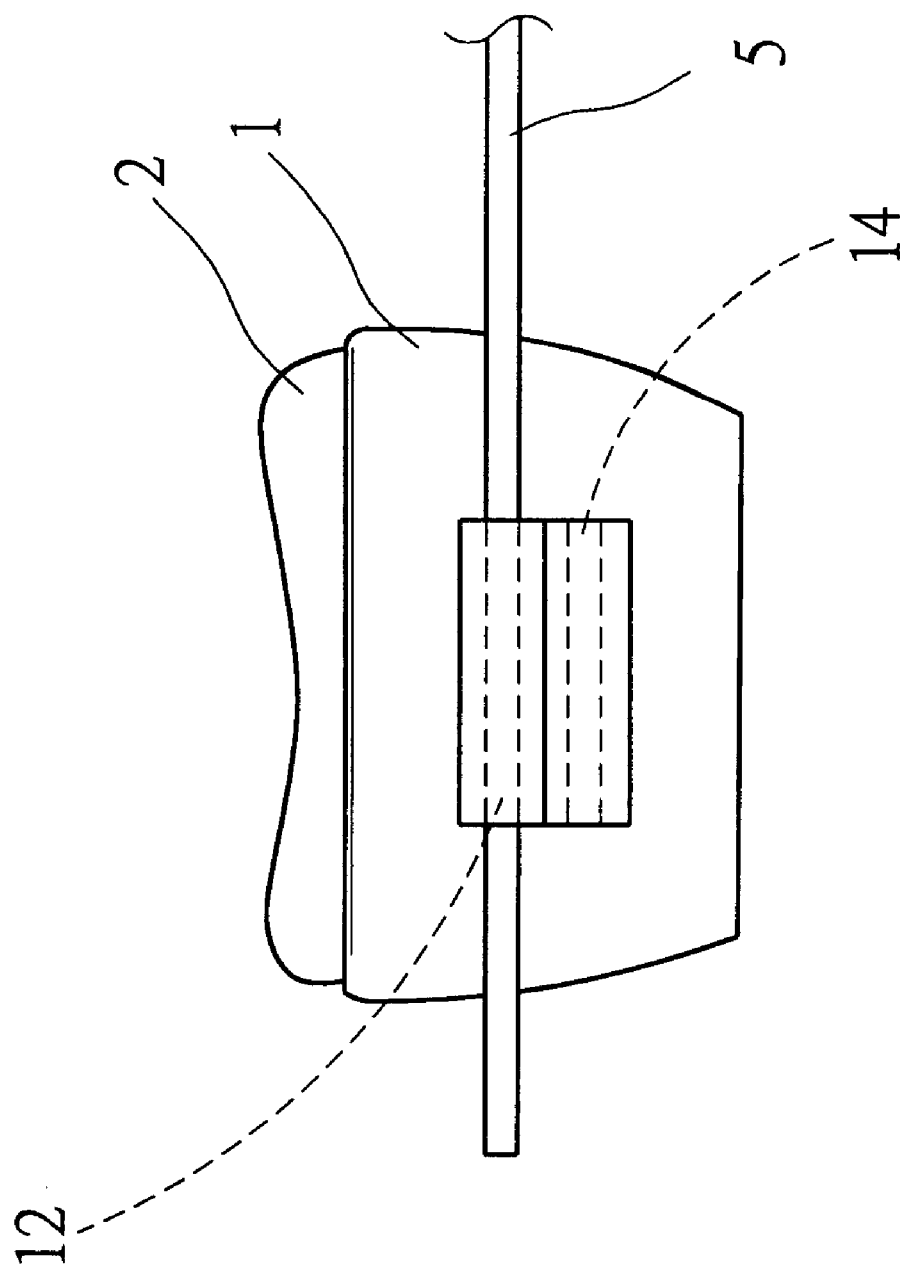
FIG. 3B is an enlarged fragmentary view of FIG. 3A showing the barrel band of the present invention.
Figure 4:
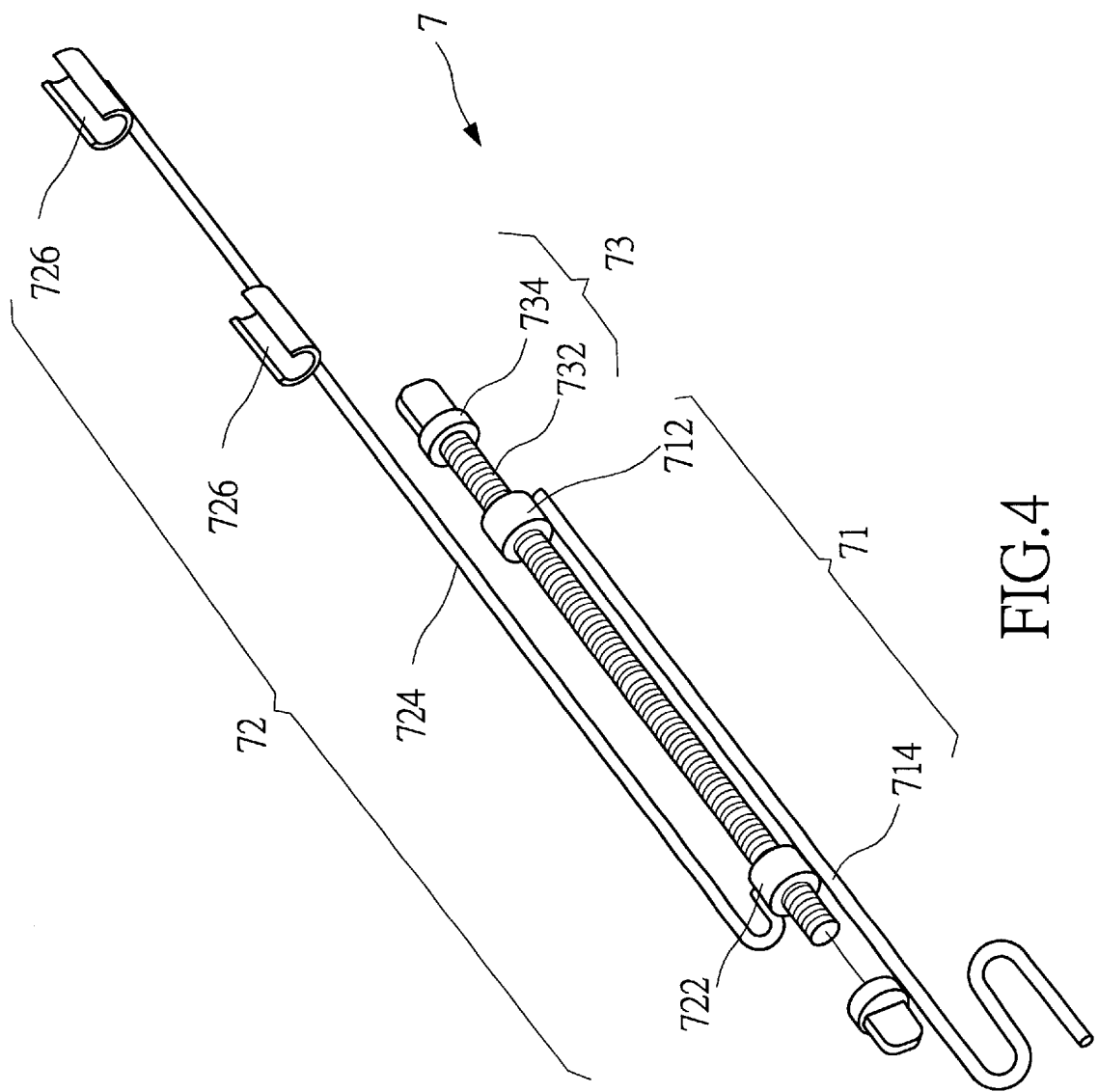
FIG. 4 is a fragmentary perspective view of the second embodiment shown in FIG. 3.

FIGS. 3A, 3B and 4 show a second embodiment of this invention. It mostly constructed like the one shown in FIGS. 1A, 1B and 2. However the hook 714 in this embodiment is more like a S-shaped hook 714 rather than C-shaped. The round hole member 712 and the S-shaped hook 714 are located on the front joint member 71, and the screw body 722 and a plurality of holding members 726 are located on the rear joint member 72 which has a linking bar 724 for engaging with the screw body 722 at one end thereof and for engaging with the holding members 726 at another end thereof. The screw bar 73 also has a screw bar stem 732 and a screw head 734 for turning and moving the rear joint member 72 toward or away from the front joint member 71 and to move the brackets 3 (and the anterior teeth 4) for orthodontic treatment. Since the hook 714 is S-shaped, therefore it is capable to "push" the brackets 3 together with the teeth 4 away from the molar 2 to correct teeth which are too crowded.

The dental distractor of this invention may be made of alloy of stable property and high strength. The screw bar enables the teeth be pulled or pushed and moved at a constant displacement easily by the patient without going to the orthodontist. The treatment is more effective and total treatment time may be greatly reduced. It thus may save a lot of cost and time for the patient.

It may thus be sent that the objects of the present invention set forth herein, as well as those made apparent from the foregoing description, are efficiently attained. While the preferred embodiments of the invention have been set forth for purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A dental distractor for rapid orthodontic movement comprising:
   a) two spaced apart barrel bands configured to be attached to two spaced apart molars, each barrel band having a steel bore and an engaging bore;
   b) a plurality of brackets configured to be attached to anterior teeth and located between the spaced apart barrel bands, each bracket having a steel wire slot;
   c) a steel wire engaging the steel bores in the barrel bands and the steel wire slots in the brackets;
   d) a threaded screw bar;
   e) a single first joint member having a screw body threadingly engaged with the threaded screw bar and a C-shaped hook extending therefrom, the C-shaped hook engaging the engaging bore of one of the two barrel bands; and,
   f) a single second joint member having a hole member threadingly engaged with the threaded screw bar, and a holding member having a C-shaped cross-sectional configuration connected to the hole member by an elongated rod, the holding member engaging the steel wire and one of the plurality of brackets.

2. A dental distractor for rapid orthodontic movement comprising:
   a) two spaced apart barrel bands configured to be attached to two spaced apart molars, each barrel band having a steel bore and an engaging bore;
   b) a plurality of brackets configured to be attached to anterior teeth and located between the spaced apart barrel bands, each bracket having a steel wire slot;
   c) a steel wire engaging the steel bores in the barrel bands and the steel wire slots in the brackets;
   d) a threaded screw bar;
   e) a single first joint member having a round hole member threadingly engaged with the threaded screw bar, and an S-shaped hook extending therefrom and engaging the engaging bore in one of the two barrel bands; and,
   f) a single second joint member having a screw body threadingly engaged with the threaded screw bar and a plurality of holding members connected to the screw body by an elongated rod, each holding member having a C-shaped cross-sectional configuration, and engaging the steel wire and one of the plurality of brackets.

* * * * *